United States Patent [19]

Dyer

[11] 4,256,649
[45] Mar. 17, 1981

[54] SYNTHESIS OF OLEFINIC OXIDES FROM OLEFIN AND OXYGEN

[75] Inventor: Paul N. Dyer, Horsham, England

[73] Assignee: Air Products and Chemicals, Inc., Allentown, Pa.

[21] Appl. No.: 923,280

[22] Filed: Jul. 10, 1978

Related U.S. Application Data

[63] Continuation-in-part of Ser. No. 844,039, Oct. 20, 1977, abandoned.

[51] Int. Cl.$^3$ .......................................... C07D 301/06
[52] U.S. Cl. ................................................ 260/348.33
[58] Field of Search .................................... 260/348.33

[56] References Cited

U.S. PATENT DOCUMENTS

| 2,776,301 | 1/1957 | Payne et al. | 260/348.31 |
|---|---|---|---|
| 3,993,673 | 11/1976 | McMullen | 260/348.31 |

FOREIGN PATENT DOCUMENTS

| 2710279 | 9/1977 | Fed. Rep. of Germany. |
|---|---|---|
| 2746812 | 4/1978 | Fed. Rep. of Germany. |
| 46-9691 | 3/1971 | Japan. |
| 46-42089 | 12/1971 | Japan. |
| 1206166 | 9/1970 | United Kingdom. |

OTHER PUBLICATIONS

A. Fusi et al., Jour. of Organometallic Chem., vol. 26 (1971), pp. 426–427.
James E. Lyons et al., Tetrahedron Letters No. 29 (1972), pp. 12903–12906.
Lyons, J. E., Advances in Chemistry Series, Homogeneous Catalysis–II, pp. 64–68, 73.
Lyons, J. E., et al., J. Org. Chem., vol. 37, No. 18 (1972), pp. 2881–2884.

*Primary Examiner*—Norma S. Milestone
*Attorney, Agent, or Firm*—E. Eugene Innis; Richard A. Dannells, Jr.

[57] ABSTRACT

Propylene oxide and other olefinic oxides are synthesized by reacting an olefin and oxygen in the presence of a catalytic amount of a complex. The complex is of the type $L_2MX_2$, $L_2M$ or $L_2MR$ where M is palladium, X is an acidic anion (preferably chloride); R is an olefinic group (preferably a propylene group) and $L_2$ consists of two monodentate ligands or a single bidentate ligand.

$L_2$:

(a) is resistant to oxidation under the conditions of the process;
(b) is of the type $AR_1R_2R_3$ or $R_4R_5AR_6AR_7R_8$ where A is phosphorous or arsenic and $R_1$, $R_2$, $R_3$, $R_4$, $R_5$, $R_6$, $R_7$ and $R_8$ are as defined herein;
(c) (in the case of a monodentate ligand) has a cone angle not less than 170° when A is phosphorous and has a cone angle not less than 142° when A is arsenic; or
(d) in the case of a bidentate ligand) the monodentate equivalent of each part of the bidentate ligand has a cone angle of not less than 170° when A is phosphorous and of not less than 142° when A is arsenic.

Increased yields of olefinic oxide may be obtained by the introduction of hydrogen.

4 Claims, No Drawings

SYNTHESIS OF OLEFINIC OXIDES FROM OLEFIN AND OXYGEN

This application is a continuation-in-part of my application Ser. No. 844,039 filed Oct. 20, 1977, now abandoned.

BACKGROUND OF THE INVENTION

1. Field of the Invention

This invention relates to a method of manufacturing an olefinic oxide from an olefin and oxygen.

Although ethylene can be oxidized to ethylene oxide at elevated temperatures in the presence of a silver catalyst, the yields of olefinic oxide from higher olefins are low.

2. Prior Art

Several indirect but more selective methods of oxidizing olefins have therefore been developed, two of which are believed to be currently in use, viz:

1. In the chlorohydrin process (U.S. Pat. No. 3,277,189), olefin is reacted with chlorine in the presence of water to give olefin chlorohydrin, which is further reacted with base to give the olefinic oxide. The disadvantage of this process is that inorganic chlorides and hydrogen chloride are also produced. Various ways of utilizing the inorganic chlorides have been proposed (for example as described in British Patent Specification No. 1,425,022) but even this process has the disadvantage of the high cost of electrical energy and cell inefficiencies.

2. In another process, more particularly described in U.S. Pat. No. 3,360,584, propylene oxide is produced in 80% yield by reaction of propylene with tertiary butyl hydroperoxide, itself produced by liquid phase oxidation of i-butane. Although a high yield is obtained, capital costs are high since the process is multistage, a complex distillation is involved in product separation and the economics are affected by the market price for the by-products, t-butanol or i-butene. Byproduct recycle is possible but consumes hydrogen.

In a proposed process, more particularly described in U.S. Pat. No. 3,806,467, olefins are oxidized by a catalytic reaction with hydrogen peroxide. This process suffers from the disadvantage that the use of hydrogen peroxide as oxidizing agent leads either to high capital costs for the process, as with the organic hydroperoxide route, or high chemical costs since it is expensive to produce by current industrial processes, and needs to be concentrated if used as an aqueous solution.

Several processes have been proposed for the direct liquid phase epoxidation of olefins higher than ethylene, e.g. U.S. Pat. Nos. 3,856,826 and 3,856,827 and Erdoel Kohle 25 584 (72). These processes involve contacting the olefin, dissolved in a suitable solvent, with oxygen at elevated temperature and pressure, in the presence of a catalyst, usually an organic complex of molybdenum. However, selectivity for the olefin oxide is at best 50-60% in these processes, even at low conversions.

British Pat. No. 1,206,166 discloses a method for catalyzing the reaction of oxygen with olefins in the liquid phase using as catalyst a complex of a Group 8 metal capable of reversibly forming an adduct with oxygen. In particular, Ir (P Ph$_3$)$_2$ CO Cl, Rh (P Ph$_3$)$_3$ I and Rh (P Ph$_3$)$_3$ Cl are used as catalysts. No examples are given for olefins lower than C$_6$, for which the selectivity is only 26%.

Other published work gives results for the dioxygen complexes (P Ph$_3$)$_2$ MO$_2$ (M=Pd or Pt) which used as olefin epoxidation catalysts. According to one source (J. Organometallic Chem. 26 417 (71)), the platinum complex does catalyze the oxidation of cyclohexene by initiating a free radical reaction, thus accounting for a distribution of products and a low selectivity to the epoxide of 1-3%. R. Sheldon and J. Van Doorn (J. Organometallic Chem. 94 115 (75)) find that there is no direct reaction between these two complexes and simple olefins such as cyclohexene at 60° C.

SUMMARY OF THE INVENTION

In contrast to the work described above, the inventor has found that, surprisingly, the direct epoxidation of olefins, especially low molecular weight linear olefins, can be catalyzed by certain complexes of palladium with good selectivity and yield.

According to one embodiment of the present invention, there is provided in a process for manufacturing an olefinic oxide which process comprises the steps of bringing an olefin and molecular oxygen into contact in the presence of a catalytic amount of a complex, the improvement comprising selecting said complex from the group consisting of L$_2$MX$_2$, L$_2$M and L$_2$MR where:

L$_2$ consists of two monodentate ligands each of which:

(a) is resistant to oxidation under the conditions of the process;

(b) is of the type AR$_1$R$_2$R$_3$ where A is selected from the group consisting of phosphorous and arsenic, and R$_1$, R$_2$ and R$_3$ independently represent alkyl, cycloalkyl, aryl or halogenoaryl groups, halogen or hydrogen; and (c) has a cone angle of not less than 170° when A is phosphorous and has a cone angle of not less than 142° when A is arsenic;

M is palladium;

X is an acidic anion; and

R is an olefinic group.

According to another embodiment of the present invention, there is provided in a process for manufacturing an olefinic oxide which process comprises the steps of bringing an olefin and molecular oxygen into contact in the presence of a catalytic amount of a complex, the improvement comprising selecting said complex from the group consisting of L$_2$MX$_2$, L$_2$M and L$_2$MR where:

L$_2$ consists of a single bidentate ligand which:

(a) is resistant to oxidation under the conditions of the process;

(b) is of the type R$_4$ R$_5$ A$_1$ R$_6$ A$_2$ R$_7$ R$_8$ where A$_1$ and A$_2$ are each selected from the group consisting of phosphorous and arsenic and R$_4$, R$_5$, R$_7$ and R$_8$ independently represent alkyl, cycloalkyl, aryl or halogenoaryl groups, halogen or hydrogen and R$_6$ represents a bivalent group derived from an alkyl, cycloalkyl, aryl or halogenoaryl groups; and (c) the monodentate equivalent of each part of said ligand selected from the group consisting of (R$_4$)$_2$ R$_5$A$_1$, R$_4$(R$_5$)$_2$A$_1$, (R$_6$)$_2$R$_7$A$_2$ and R$_6$(R$_7$)$_2$A$_2$ has a cone angle not less than 170° when A$_1$ and A$_2$ are phosphorous and a cone angle not less than 142° when A$_1$ and A$_2$ are arsenic.

The oxygen may be pure or may comprise part of a gaseous mixture, e.g. air.

PREFERRED EMBODIMENTS

Preferably the alkyl group in the foregoing formulas has from 1 to 6 carbon atoms; the cycloalkyl group has from 5 to 8 carbon atoms and is more preferably cyclohexyl; the aryl group is phenyl; the halogenoaryl group is fluorinated and more preferably is perflorinated. Still more preferably the halogenoaryl group is pentafluorophenyl. The halogen is iodine, fluorine, bromine or preferably chlorine.

Particularly preferred mondentate ligands are tri(pentafluorophenyl) phosphine having a cone angle of 184°, tricyclohexylphosphine having a cone angle of 170° or triphenylarsine having a cone angle of 142°. The preferred bidentate ligand is 1,2-bis(diperfluorophenylphosphine) perfluorobenzene.

R is preferably an ethylene or propylene group.

Preferably the acidic anion is a halide, preferably chlorine. It may however, be for example, acetate.

The preferred complexes are bis(tri(pentafluorophenyl) phosphine) palladium dichloride; bis(tri(pentafluorophenyl)phosphine) palladium; bis(tricyclohexylphosphine) palladium; (1,2-bis(diperfluorophenylphosphino)perfluorobenzene) palladium dichloride; (1,2-bis(diperfluorophenylphosphine)perfluorobenzene) palladium; ethylene bis(tricyclohexylphosphine) palladium; propylene bis(tri(pentafluorophenyl)phosphine) palladium; or propylene (1,2-bis(diperfluorophenylphosphino) perfluorbenzene palladium.

If desired, hydrogen may be brought into contact with the olefin and molecular oxygen.

The olefin, oxygen and complex can be contacted in various ways, for example the complex may be dissolved in an organic liquid and the olefin (in gaseous form) and oxygen sparged through the liquid. The olefinic oxide may be separated by conventional techniques, for example by distillation or condensation from the effluent gas stream.

Alternatively the complex may be dissolved in an organic liquid and water added. If the two are immiscible and the olefinic oxide is soluble in water, the olefinic oxide formed when the gas mixture is bubbled through the system may be separated from the reaction system by extraction in the aqueous phase. If the organic liquid and water are miscible or partially miscible, the maximum amount of water that may be present in the system is limited by the constraint of catalyst solubility. Examples of suitable solvents (which should not react with olefin, oxygen or hydrogen, under the conditions of the process) which are miscible with water, are 2-methylpropan-2-ol and propan-2-ol. Suitable solvents which are immiscible with water are 1,2-dichlorobenzene, chlorobenzene and xylene.

In a further method of preparation, the catalyst is dissolved in the olefin (in liquid form) and oxygen, or oxygen and hydrogen, is bubbled through the solution.

Alternatively the complex may be conventionally supported, or heterogenized by using as one or both of the ligands, a ligand grouping chemically attached to a suitable polymer. A particularly preferred example is the catalyst obtained using L of the type:

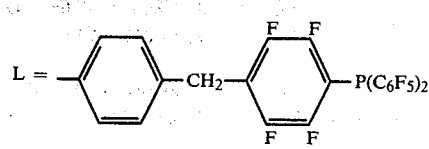

where the hatched vertical line represents a polymer or copolymer (e.g. a styrene-divinylbenzene copolymer). The complex supported or heterogenized in this way could either be used flooded with an organic liquid, or simply be brought into contact with a gaseous mixture of olefin and oxygen, or olefin, oxygen and hydrogen, and the products, for example, cooled to condense the olefinic oxide.

In all modes of operation of this invention, the gas mixture used is preferably one which does not support ignition under the process conditions. This includes mixtures of olefin and oxygen, or olefin, hydrogen and oxygen made non-ignitable by dilution with a carrier gas, for example nitrogen and/or methane.

The process is advantageously operated at super atmospheric pressure, for example up to 1000 psig and at temperatures up to 200° C.

The invention is illustrated in the following nonlimiting Examples in which all percentages are by volume unless otherwise stated.

EXAMPLE 1

100 ml of a solution of $4.1 \times 10^{-3}$ molar Pd $Cl_2$ $(P(C_6F_5)_3)_2$ in 2-methylpropan-2-ol was placed in a Pyrex (Trade Mark) flask equipped with a reflux condenser and gas sparger tube. The solution in the flask was heated to 54° C. and 0.56 Nl/m of a non-flammable mixture of 29% air in propylene was bubbled through the solution at atmospheric pressure. Samples of the gas leaving the top of the reflux condenser at 20° C. were analyzed by GLC (gas-liquid chromatography) and found to contain no $CO_2$, no acetone and 0.03% propylene oxide. Selectivity was better than 60%.

EXAMPLE 2

200 ml of a solution of $4.2 \times 10^{-3}$ molar Pd $Cl_2$ $(P(C_6F_5)_3)_2$ in 1,2-dichlorobenzene were placed in a Pyrex vessel equipped with a reflux condenser and perforated Teflon (Trade Mark) disc sparger. A non-flammable gas mixture of 3% oxygen in propylene at 85 psig was bubbled through the solution at 89° C. and a flow rate of 1.8 actual l/m. Samples of gas leaving the top of the condenser at 19° C. were analyzed by GLC. It was found that propylene oxide was produced at a rate of 1.0 moles/mole catalyst/hour. Selectivity was better than 60%.

EXAMPLE 3

100 ml of a solution of $8.1 \times 10^{-3}$ molar Pd $Cl_2(P(C_6F_5)_3)_2$ in 1,2-dichlorobenzene plus 100 ml of deionized water were placed in a Pyrex vessel equipped with a reflux condenser and a perforated Teflon disc sparger. A non-flammable gas mixture of 43.1% propylene, 54.4% hydrogen and 2.5% oxygen was bubble through the solution at a total pressure of 225 psig and 3.6 actual l/m at 67° C. Samples of gas leaving the top of the condenser at 19° C. were analyzed by GLC. It was found that propylene oxide was produced at a rate of 5.11 moles/mole catalyst/hour with no $CO_2$. Selectively was better than 60%.

EXAMPLE 4

100 ml of a solution of $1.7 \times 10^{-3}$ molar $PdCl_2$ $(P(C_6F_5)_3)_2$ in 2-methylpropan-2-ol was placed in a Pyrex flask equipped with a reflux condenser and gas sparger tube. The solution in the flask was heated to 29° C. and 0.85 Nl/m of a nonflammable mixture of 2.1% oxygen in propylene and was bubbled through the solution at atmospheric pressure. Samples of the gas leaving the top of the reflux condensr at 18° C. were analyzed by GLC and found to contain no $CO_2$, no acetone and 0.21% propylene oxide. Selectivity was better than 60%.

What is claimed is:

1. In a process for manufacturing an olefinic oxide which process comprises the steps of bringing an olefin and molecular oxygen into contact in the presence of a catalytic amount of a solution of a complex at temperatures of up to 200° C. and pressures up to 1000 psig, the improvement comprises selecting and dissolving in an organic liquid said complex from the group consisting of bis(tricyclohexylphosphine palladium dichloride; bis(tripentafluorophenyl)phosphine) palladium dichloride; bis(tri(pentafluorophenyl)phosphine)palladium; bis(tricyclohexylphosphine) palladium; ethylene bis(tricyclohexylphosphine) palladium; and propylene bis(tri(pentafluorophenyl)phosphine) palladium.

2. In a process for manufacturing an olefinic oxide which process comprises the steps of bringing an olefin and molecular oxygen into contact in the presence of a catalytic amount of a solution of a complex at temperatures of up to 200° C. and pressures up to 1000 psig, the improvement comprises selecting and dissolving in an organic liquid said complex from the group consisting of (1,2-bis(diperfluorophenylphosphino)perfluorobenzene) palladium dichloride; (1,2-bis(diperfluorophenylphosphino) perfluorobenzene) palladium; and propylene (1,2-bis(diperfluorophenylphosphino) perfluorbenzene palladium.

3. The process of claim 1 wherein said complex is bis(tri(pentafluorophenyl) phosphine) palladium dichloride.

4. The process of claim 2 wherein said complex is (1,2 bis-(diperfluorophenylphosphino) perfluorobenzene) palladium dichloride.

* * * * *